United States Patent
Nesa et al.

(10) Patent No.: US 10,031,072 B2
(45) Date of Patent: Jul. 24, 2018

(54) HEATING DEVICE FOR SPECTROMETRY MEASUREMENT APPARATUS

(71) Applicant: OLYTHE, Aix-en-Provence (FR)

(72) Inventors: Guillaume Nesa, Aix-en-Provence (FR); Grégory Dubois, Maisons-Laffitte (FR); Etienne Flesch, Andresy (FR); Lionel Pafumi, Vitrolles (FR); Jean-Pierre Thierry, Andresy (FR)

(73) Assignee: OLYTHE, Aix-en-Provence (FR)

( * ) Notice: Subject to any disclaimer, the term of this patent is extended or adjusted under 35 U.S.C. 154(b) by 8 days.

(21) Appl. No.: 15/023,143

(22) PCT Filed: Sep. 18, 2014

(86) PCT No.: PCT/FR2014/052319
§ 371 (c)(1),
(2) Date: Mar. 18, 2016

(87) PCT Pub. No.: WO2015/040329
PCT Pub. Date: Mar. 26, 2015

(65) Prior Publication Data
US 2016/0231228 A1    Aug. 11, 2016

(30) Foreign Application Priority Data

Sep. 18, 2013 (FR) ..................... 13 58964

(51) Int. Cl.
*G01N 21/17* (2006.01)
*G01N 21/35* (2014.01)
(Continued)

(52) U.S. Cl.
CPC ........... *G01N 21/255* (2013.01); *G01N 21/01* (2013.01); *G01N 21/0332* (2013.01);
(Continued)

(58) Field of Classification Search
CPC .... G01N 21/00; G01N 21/01; G01N 21/0332; G01N 21/05; G01N 21/15; G01N 21/17;
(Continued)

(56) References Cited

U.S. PATENT DOCUMENTS

| | | | | |
|---|---|---|---|---|
| 4,205,913 A * | 6/1980 | Ehrfeld | .............. | G01N 21/3504 250/340 |
| 5,793,043 A * | 8/1998 | Weckstrom | ........ | G01N 33/4972 250/339.13 |
| 6,222,160 B1 * | 4/2001 | Remke | ................... | A45C 11/20 219/387 |
| 2003/0091089 A1 * | 5/2003 | Krausse | ................. | G02B 7/008 374/16 |
| 2006/0011842 A1 * | 1/2006 | Minuth | .............. | G01N 21/3151 250/339.13 |

(Continued)

FOREIGN PATENT DOCUMENTS

| | | | | |
|---|---|---|---|---|
| CN | 201282572 Y | 7/2009 | | |
| DE | 102005027237 B3 * | 1/2007 | ......... | G01N 21/0332 |

(Continued)

OTHER PUBLICATIONS

International Search Report issued in corresponding PCT/FR2014/052319 dated Dec. 22, 2014; 3pgs.

*Primary Examiner* — Nguyen Ha
(74) *Attorney, Agent, or Firm* — Maier & Maier, PLLC

(57) ABSTRACT

A heating device for a spectrometry measurement apparatus, wherein it is in the form of a supple optical article, the article comprising a supple flexible support having a top face and a bottom face, the top face being covered with a reflective material in order to form an optical-reflection layer, a flexible heating element being disposed on at least one of the faces of the support.

11 Claims, 2 Drawing Sheets

(51) Int. Cl.
*G01N 33/497* (2006.01)
*H05B 3/34* (2006.01)
*G01N 21/25* (2006.01)
*G01N 21/3504* (2014.01)
*G01N 21/01* (2006.01)
*G01N 21/03* (2006.01)
*G01N 21/05* (2006.01)
*G01N 21/15* (2006.01)

(52) U.S. Cl.
CPC ............ *G01N 21/05* (2013.01); *G01N 21/15* (2013.01); *G01N 21/3504* (2013.01); *G01N 33/4972* (2013.01); *H05B 3/34* (2013.01); *G01N 2021/158* (2013.01); *G01N 2201/0231* (2013.01); *G01N 2201/068* (2013.01)

(58) Field of Classification Search
CPC .. G01N 21/225; G01N 21/35; G01N 21/3504; G01N 2201/0231; G01N 2201/068; G01N 2201/158; G01N 33/497; G01N 33/4972; H05B 3/34
See application file for complete search history.

(56) References Cited

U.S. PATENT DOCUMENTS

| | | | |
|---|---|---|---|
| 2006/0033027 A1* | 2/2006 | Fischer | G01N 21/15 250/343 |
| 2009/0000620 A1* | 1/2009 | Virr | A61M 16/1075 128/203.27 |
| 2011/0084820 A1 | 4/2011 | Walter | |
| 2012/0190997 A1* | 7/2012 | Varga | G01N 21/031 600/532 |
| 2013/0074577 A1* | 3/2013 | Nesa | G01N 21/0332 73/23.3 |
| 2016/0238516 A1* | 8/2016 | Nesa | G01N 21/3504 |
| 2017/0219480 A1* | 8/2017 | Nesa | G01N 15/1475 |

FOREIGN PATENT DOCUMENTS

| | | |
|---|---|---|
| FR | 2941530 A1 | 7/2010 |
| JP | 2012177690 A | 9/2012 |
| WO | 02096290 A1 | 12/2002 |
| WO | 2011042679 A1 | 4/2011 |

* cited by examiner

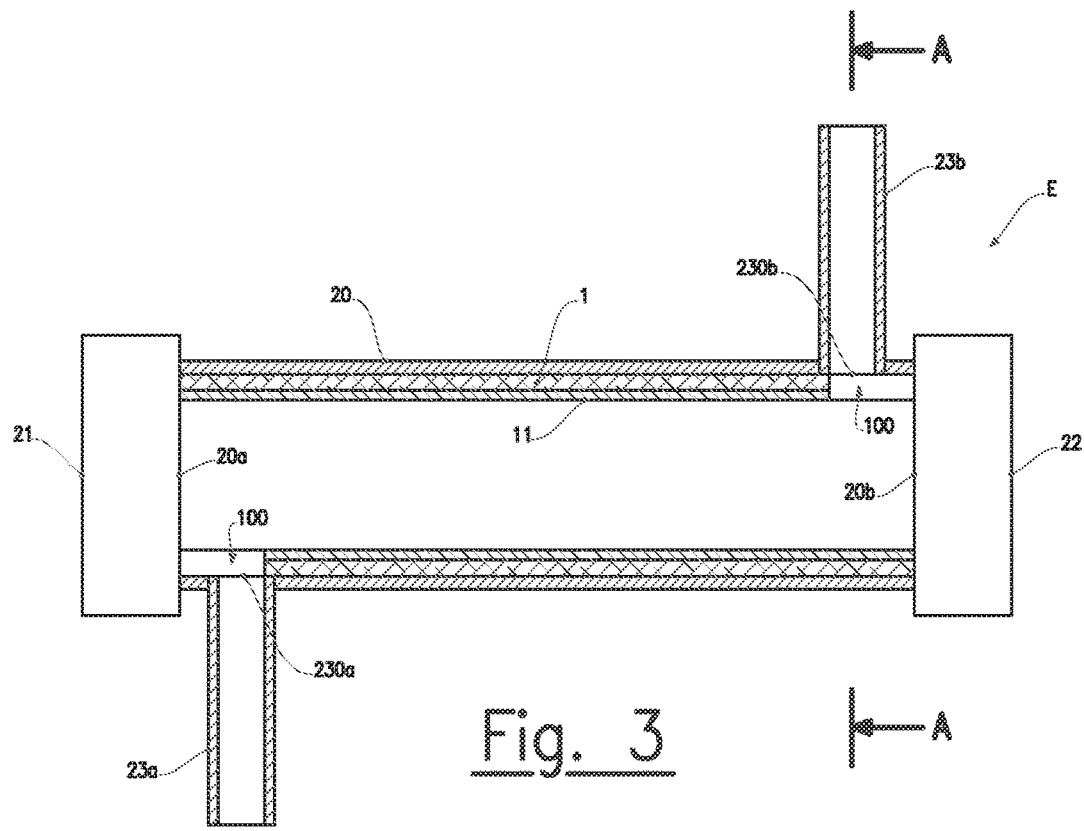
Fig. 3
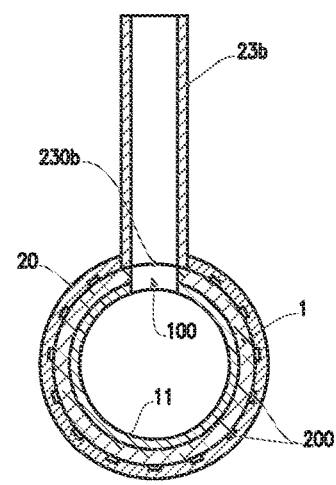
Fig. 4 (A-A)

HEATING DEVICE FOR SPECTROMETRY MEASUREMENT APPARATUS

TECHNICAL FIELD OF THE INVENTION

The subject matter of the invention is a heating device for a spectrometry measurement device. Another subject matter of the invention is a spectrometry measurement apparatus integrating such a device. Another subject matter is a breathalyzer for measuring or detecting a partial gas level exhaled by a breath fluid and the measuring vessel of which integrates such a device. The final subject matter thereof is a method for manufacturing a measuring vessel of a breathalyzer in which this device is inserted.

The invention relates to the technical field of elements constituting spectrometry measurement appliances and more particularly elements integrated in the measuring cell thereof. They also concern the technical field of portable electronic devices, such as breathalyzers for example, for measuring or detecting a partial gas level exhaled by a breath fluid.

PRIOR ART

A breathalyzer comprising a device emitting infrared radiation, an infrared receiver and a measuring vessel in which the breath fluid for which a partial gas level must be measured or detected circulates is known through the patent document FR 2.941.530 (SERES ENVIRONNEMENT), hereinafter "SERES document". The measuring vessel is in the form of a hollow tube, the internal surface of which is provided with a reflective material forming an optical reflection layer. This document teaches associating the hollow tube with a heating means. The latter makes it possible to raise the tube to a temperature of approximately 39° C. in order to prevent any formation of condensation on its internal wall when the breath fluid is flowing. This is because condensation inside the tube impairs the reflective quality of the reflective layer and does not allow optimum recovery, at the infrared receiver, of the radiation emitted by the emission device.

The SERES document makes provision for coiling a heating element on the external surface of the tube. Though this arrangement provides heating of the tube, there is nevertheless a great thermal loss. As a result electrical consumption is not insignificant, especially in the case of a portable apparatus where the greatest energy autonomy is required. Furthermore, positioning the heating element around the tube is not easy and the contact between element and tube is not assured. An uneven heating temperature on the internal surface of the tube results, and this disparity may influence the optical path and therefore the final measurement.

The invention aims to remedy this state of affairs. In particular, one objective of the invention is to propose a heating device that is more economical in terms of electrical consumption while keeping the same optical quality.

Another objective of the invention is to propose a heating device that is simpler and quicker to install than the one described in the SERES document.

Yet another objective of the invention is to propose a heating device that can heat the hollow tube of the measuring vessel more rapidly and evenly.

An addition objective of the invention is to propose a heating device that can be adapted to any type of spectrometry measurement apparatus.

DISCLOSURE OF THE INVENTION

The solution proposed by the invention is a heating device remarkable in that it is in the form of a supple optical article comprising a supple flexible support and having a top face and a bottom face. The top face is covered with a reflective material to form an optical-reflection layer. A flexible heating element is disposed on at least one of the faces of the support.

This optical article can easily and quickly be inserted in the hollow tube of the measuring vessel so that the reflective material of said article forms the optical-reflection layer. The flexible heating element forms the heating means and replaces the heating electric element provided in the SERES document. This flexible optical article therefore has a dual function: firstly, providing optical reflection and secondly, heating the reflective surface. Since the heating element is now disposed actually inside the hollow tube, thermal loss is reduced, or even negligible, which is beneficial in terms of reducing electrical consumption. Furthermore, it was found that the temperature rise inside the hollow tube was more rapid than with the heating device of the SERES document, and that the distribution of the temperature was more homogeneous.

The patent document CN 201.282.572 (JIANBO LIANG) relates to a supple heating film with a face of the radiant type. This film can be used in a large number of fields, such as daily hygiene or health, and for preserving heat, protection against frost or damp for agricultural animal husbandry, personal domestic electrical equipment and pipes, and may be employed in a variety of places in which the temperature is low, medium or high. This heating film is however not suitable for being used for a spectrometry measurement apparatus. In any event, the sole function of the reflective layer described in this patent document is reflecting the thermal radiation emitted for the heating filament, in order to avoid thermal losses. In no case is this layer used for providing optical reflection.

The patent document WO 2011/042679 (AUTOLIV) does not disclose a supple flexible support.

Other advantageous features of the heating device that is the subject matter of the invention are listed below, each of these features being able to be considered alone or in combination with the remarkable features defined above:

The heating element may be disposed on the bottom face of the flexible support.

The heating element may also be disposed on the top face of the flexible support, the reflective material covering said heating element.

The heating element is preferentially in the form of a flexible printed circuit installed on one face of the support, and in which one or more heating filaments are integrated.

The flexible printed circuit is preferentially associated with a layer of a heat-conductive material.

The heat-conductive material may preferentially be chosen from the following group: copper, aluminum, silver, gold, etc.

The supple flexible support is advantageously produced from a material chosen from the following group: polyimide, polyepoxide, polyester, epoxy resin reinforced with glass fibers.

This supple flexible support preferentially has a thickness of between 1 µm and 250 µm.

The reflective material forming the optical-reflection layer is advantageously chosen from the following group: gold, cobalt, silver, nickel, copper, aluminum, chrome, zinc, silica.

Another aspect of the invention relates to a spectrometry measurement apparatus comprising a measuring cell, said cell being combined with the previously defined heating device.

Yet another aspect of the invention relates to a breathalyzer for measuring or detecting a partial gas level exhaled by a breath fluid, said breathalyzer comprising a device emitting infrared radiation, an infrared receiver and a measuring vessel in which the breath fluid flows, the measuring vessel being in the form of a hollow tube provided with a reflective material forming an optical-reflection layer, said tube being associated with a heating means. The heating device defined previously is inserted in the tube so that the reflective material of the supple optical article forms the optical-reflection layer, the flexible heating element forming the heating means.

Other advantageous features of the breathalyzer that is the subject matter of the invention are listed below, each of these features being able to be considered alone or in combination with the remarkable features defined above:

The hollow tube forming a measuring vessel preferentially has a length of less than or equal to 100 mm, the optical article having a length corresponding to that of said tube.

The internal surface of the hollow tube comprises elements in relief, the optical article being in contact with the internal surface of said tube only at these elements in relief.

An additional aspect of the invention relates to a method for manufacturing a measuring vessel of a breathalyzer making it possible to measure the partial gas level exhaled by a breath fluid, said measuring vessel being in the form of a hollow tube provided with a reflective material forming an optical reflection layer. This method consists of:

rolling or bending the optical article of the heating device defined above, inserting the optical article thus rolled or bent in the hollow tube so that the reflective material of said article forms the optical-reflection layer.

DESCRIPTION OF THE FIGURES

Other advantages and features of the invention will emerge more clearly from a reading of the description of a preferred embodiment that follows, with reference to the accompanying drawings, produced by way of indicative and non-limitative examples and in which:

FIG. 3 is a schematic view in longitudinal section of a breathalyzer according to the invention, FIG. 4 is a view in cross section along A-A of the breathalyzer of FIG. 3.

PREFERRED EMBODIMENTS OF THE INVENTION

The heating device that is the subject matter of the invention is particularly, but not exclusively, intended to be used in a spectrometry measurement apparatus. It is in particular designed to be combined with a measuring cell of such an apparatus. It is in particular designed to be integrated in a breathalyzer, but may also be integrated in any other apparatus that measures a parameter concentration of alcohol, CO, $CO_2$, $H_2O$, etc.), in a breath fluid or in any other fluid warmer and/or more humid than the ambient air (for example a vapor or an exhaust gas). Its main function is to maintain the fluid to be analyzed at a required temperature. For measuring breath fluid, this heating temperature, between 35° C. and 40° C., is such that the fluid does not condense.

For reasons of clarity and concision the remainder of the description refers solely to a breathalyzer, without this being able to be considered to be a limitation to the protection sought. "Breathalyzer" means, within the meaning of the present invention, any apparatus (including breath alcohol testers) for measuring or detecting a partial gas level exhaled by a breath fluid, and in particular measuring the concentration of alcohol in the expired air and/or detecting an alcohol concentration threshold in the expired air.

Figure 1:
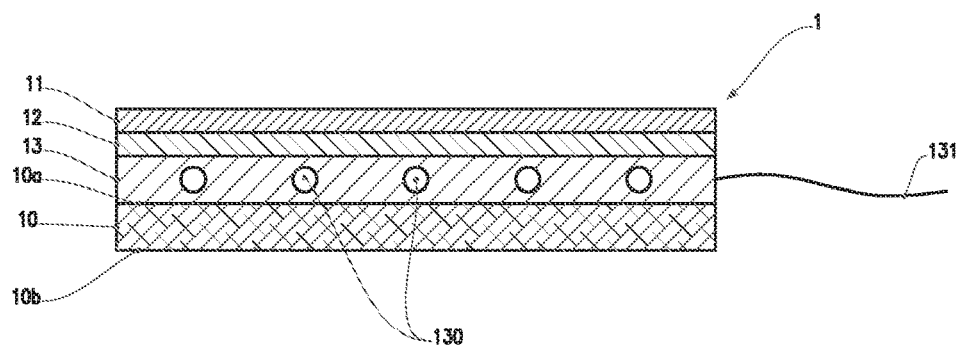
FIG. 1 is a schematic view in cross section of an optical article according to the invention.

Referring to FIG. 1, the heating device is in the form of a supple optical article 1. This article comprises a supple flexible support 10 that consist of a thin film having a thickness of between 1 μm and 250 μm, preferentially approximately 25 μm. A good suppleness/strength ratio is obtained with these thickness values. Its length and width depend on the dimensions of the measuring cell with which the heating device is combined. The support 10 is advantageously produced from a material chosen from the following group: polyimide (for example Kapton®), polyepoxide, polyester, epoxy resin reinforced with glass fiber, or aluminum substrate (for example COOL-CLAD® support marketed by the company Al TECHNOLOGY). Any other material generally used for manufacturing a supple printed circuit may however be envisaged. The support 10 may be obtained by molding, extrusion, lamination, etc.

The support 10 comprises a top face 10a and a bottom face 10b that are opposite each other. In the accompanying figures, the top face 108 is covered with a reflective material 11 in order to form an optical-reflection layer on which the infrared radiation will rebound. So that the reflection layer is as reflective as possible and in order to limit energy losses in the radiation emitted, the reflective material 11 is preferentially chosen from the following group: gold, cobalt, silver, nickel, copper, aluminum, chromium, zinc and silica.

The reflective material 11 has a thickness of between 0.01 μm and 500 μm. It may be deposited by adhesive bonding, electrochemical deposition, electrolytic deposition, printing, screen printing, vacuum metallization, heating, or by any other fine-layer adhesion method.

For the purpose of ensuring good holding in position of the reflective material 11 on the top face 10a of the support 10, an attachment layer 12 may first be deposited on this face. This layer 12 consists for example of a layer of copper, aluminum, silver or polyethylene, the thickness of which is for example between 0.1 μm and 500 μm, deposited by a fine-layer adhesion method of the type mentioned in the previous paragraph. The layer 12 is not essential and may in particular be avoided in the case where the reflective material 11 is for example deposited by electrolytic deposition.

A flexible heating element 13 is disposed on at least one of the faces 10a, 10b of the support 10. This heating element 13 may consist of a thin heating element fixed to the support 10, for example by adhesive bonding, lamination, electrochemical deposition, electrolytic deposition, printing, screen printing, vacuum metallization, heating, mechanical fixing, or by any other fine-layer adhesion method.

According to one advantageous feature of the invention, the heating element 13 is in the form of a flexible printed circuit in which one or more heating filaments 130 are integrated. The latter are for example in the form of metal bands (copper, copper-nickel, aluminum, etc.), 1 µm to 50 µm thick, placed between two layers of polyimide. One of these layers may moreover form the support 10. By way of illustrative example, it is possible to use a supple heating circuit marketed by the company MINCO, under the trademark THERMOFOIL®.

The heating element 13 is connected to conductive wires 130 that emerge from the support 10 and are intended to be connected to a current source of the cell battery type. In practice, the current source is determined so as to deliver a voltage of between 0.1 volts and 5 volts so that the power developed by the heating element 13 is between 10 mW/cm$^2$ and 2 W/cm$^2$. Temperature regulation for the heating element 13, for example around 39° C., may be provided.

For the purpose of evening out the distribution of the temperature over the entire surface of the article 1, the heating element 13 may be associated with a layer of heat-conductive material. In the accompanying FIGS. 1 and 2, for the purpose of simplifying the design and optimizing the compactness of the article 1, this layer is the aforementioned attachment layer 12, chosen in a heat-conductive material (copper, aluminum, silver, etc.). Another additional layer may however be envisaged, in particular in the case where the attachment layer is not provided.

In FIG. 1, the heating element 13 is disposed on the top face 10*a* of the support 10. It is covered with the reflective material 11, and optionally by the layer 12.

Figure 2:
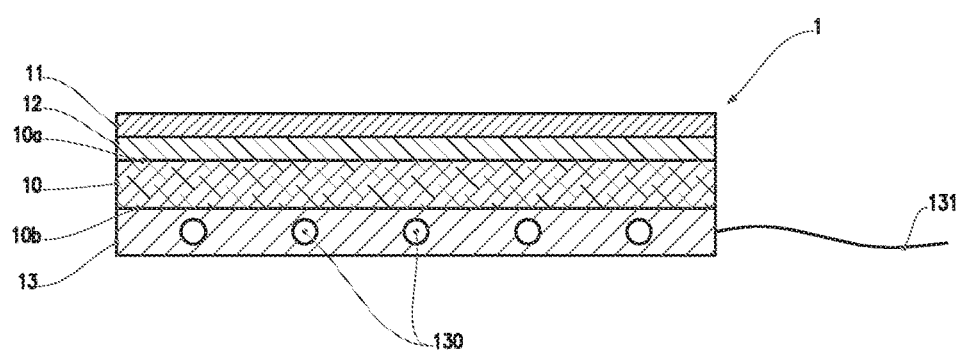
FIG. 2 is a schematic view in cross section of an optical article according to the invention, in a variant embodiment.

In FIG. 2, the heating element 13 is disposed on the bottom face 10*b* of the support 10. It is therefore situated opposite the reflective material 11. In this configuration, the support 10 fulfills a role of thermal buffer. This is because, as explained below, the fluid to be analyzed flows in the measuring vessel while being in contact with the reflective material 11, which is liable to cool abruptly. It was found that, in the configuration in FIG. 2, the reflective material 11 cooled more slowly, the support 10 increasing the thermal inertia of the article 1. Temperature regulation is thus easier and less abrupt than in the case of the configuration in FIG. 1.

The integration of the heating device in the measuring cell of a portable breathalyzer will now be detailed with reference to FIGS. 3 and 4. This breathalyzer E is of the type described in the aforementioned SERES document. It comprises a measuring vessel in the form of a hollow tube 20. The latter typically has a circular cross section but may have a square, rectangular, oval, etc. cross section. The tube 20 may be produced from metal (e.g. aluminum, stainless steel, etc.) or plastics material (e.g. PVC, ABS). It may be obtained by molding, extrusion or any other method suitable for a person skilled in the art. Its internal surface does not require any particular surface treatment, unlike the one described in the SERES document.

According to a preferred embodiment, the length of the tube 20 is between 5 mm and 200 mm, preferentially less than or equal to 100 mm, the invention making it possible to use a shorter measuring vessel than that of the SERES document. Its inside diameter is less than 15 mm, for example between 4 mm and 15 mm. And its thickness is less than 5 mm, for example between 1 mm and 5 mm.

One end 20*a* of the tube 20 is provided with a device 21 for emitting infrared radiation, advantageously in wavelengths of between 1 µm and 12 µm. The other end 20*b* is provided with an infrared receiver 22. The emitter 21 and the infrared receiver 22 are of the type known to persons skilled in the art. The breath fluid flows in the measuring vessel between the two ends 20*a*, 20*b* of the tube 20. More particularly, the fluid enters the tube 20 by means of an inlet nozzle 23*a* (in which the user blows) installed at the end 20*a*, and emerges from said tube by means of an outlet nozzle 23*b* installed at the opposite end 23*b* The two nozzles 23*a* and 23*b* may be situated on the same side of the tube 20, or on the contrary on two opposite sides (FIG. 3), or disposed at any angle. A pumping system may be associated with the nozzles 23*a* and 23*b* in order to ensure flow of the blown fluid sample.

The heating device is inserted in the tube 20 so that the reflective material 11 of the article 1 forms the optical-reflection layer. When the tube 20 has a circular cross section, the article 1 is rolled, manually or automatically, so as to form a cylinder. In the case where the tube 20 has not a circular cross section, but a square, rectangular or other polygonal-shaped cross section, the article 1 is bent so as to form a tube having this particular cross section. The reflective material 11 forms the internal surface of this cylinder (or tube). This arrangement optimizes the lengths of the optical paths in the tube 20, while keeping sufficient quantity of light as far as the receiver 22. As a result the measuring vessel may be shorter than that of the breathalyzer described in the SERES document.

The optical article 1 has a length corresponding to that of the tube 20 so that the internal surface of the latter is completely, or substantially completely, covered by said article. This is because some zones of the internal surface of the tube 20 may not be covered, in particular at the ends 20*a* and 20*b*, while keeping an acceptable measuring quality.

The article 1 thus conformed is then inserted in the tube 20, at one of the ends 20*a* or 20*b*, so that the reflective material 11 forms the optical-reflection layer against which the infrared radiation will rebound. In the configuration in FIG. 1, the support 10 is in contact with the internal surface of the tube 20. In the configuration in FIG. 2, it is the heating element 13 that is in contact with the internal surface of the tube 20.

When the article 1 is formed, it has a natural tendency to unwind (or unfold) in order to regain its original flat shape. The result of this ability is that the article 1 is naturally held in position inside the tube 20 without its being necessary to provide another mechanical fixing system or one by adhesive bonding. Such a system may however be envisaged as a precautionary measure.

In order to limit thermal losses to the outside of the tube 20, the internal surface of the latter advantageously comprises elements in relief 200. The latter consist for example of longitudinal or radial ribs, or in any other form having hollows and protrusions on the internal surface of the tube 20. As is clear in FIG. 4, when the optical article 1 is inserted in the tube 20, it is contact only with these elements in relief. The thermal bridges between the heating device and the tube 1 are in fact reduced.

Once the article 1 is formed and installed in the tube 20, and the measuring vessel is thus fabricated, the other components 21, 22, 23*a*, 23*b* are fitted.

Figure 5:
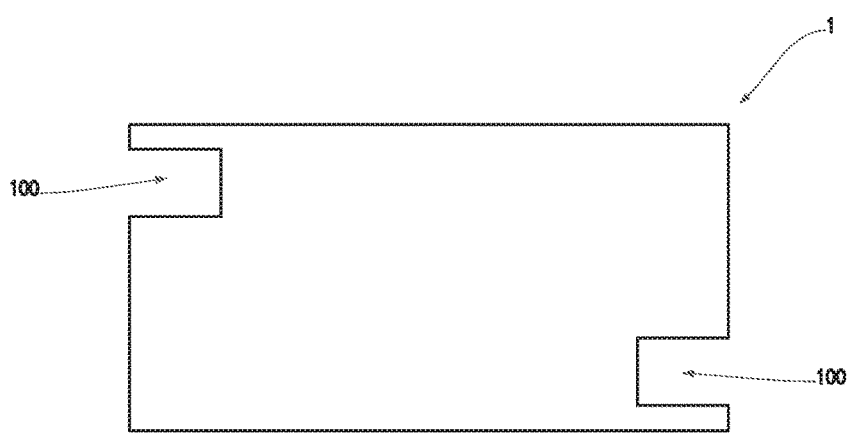
FIG. 5 is a schematic plan view of an optical article according to FIG. 1 or 2.

With regard to the nozzles 23*a*, 23*b*, it is necessary that they emerge inside the measuring vessel, despite the presence of the article 1 that covers the internal surface of the tube 20. To do this, and as will appear in FIG. 5, the article 1 comprises notches, piercings or, more generally, recesses 100, the dimensions of which are adjusted to the diameters of the nozzles 23*a*, 23*b*. These recesses 100 are situated at the lateral edges of the article 100. When the article 1 is shaped and inserted in the tube 10, the recesses 100 are placed opposite the emerging ends 230*a*, 230*b* of the nozzles 23*a*, 23*b* and leave the latter free.

The arrangement of the various elements and/or means and/or steps of the invention, in the embodiments described above, must not be understood as requiring such an arrangement in all implementations. In any event, it will be understood that various modifications may be made to these elements and/or means and/or steps without departing from the spirit and scope of the invention. In particular, the heating device according to the invention may be combined with a measuring cell processing signals other than infrared signals and/or by an analysis technique other than spectrometry.

The invention claimed is:

1. A method for manufacturing a measuring vessel of a breathalyzer making it possible to measure a partial gas level exhaled by a breath fluid, the measuring vessel being in the form of a hollow tube provided with a reflective material forming an optical-reflection layer, the method comprising:
   using a supple optical article, the supple optical article comprising a supple flexible support having a top face and a bottom face;
   covering the top face of the optical article with a reflective material in order to form the optical-reflection layer;
   disposing a flexible heating element on at least one of the faces of the support;
   rolling or bending the optical article comprising the support with the optical-reflection layer and the heating element so as to form a tube having a cross section similar to that of the hollow tube; and
   inserting the rolled or bent tube into the hollow tube such that the optical-reflection layer is exposed inside the hollow tube.

2. The method according to claim 1, wherein the heating element is disposed on the bottom face of the support.

3. The method according to claim 1, further comprising: covering the heating element with the reflective material, wherein the heating element is disposed on the top face of the support.

4. The method according to claim 1, further comprising: using a flexible printed circuit in which one or more heating filaments are integrated to form the heating element.

5. The method according to claim 1, further comprising: associating the heating element with a layer of a heat-conductive material.

6. The method according to claim 5, wherein the heat-conductive material is chosen from a group consisting of copper, aluminum, silver, and gold.

7. The method according to claim 1, wherein the support is produced from a material chosen from a group consisting of polyimide, polyepoxide, polyester, epoxy resin reinforced with glass fiber, and aluminum substrate.

8. The method according to claim 1, wherein the support has a thickness of between 1 µm and 250 µm.

9. The method according to claim 1, wherein the reflective material forming the optical-reflection layer is chosen from a group consisting of gold, cobalt, silver, nickel, copper, aluminum, chromium, zinc, and silica.

10. The method according to claim 1, wherein the hollow tube forming the measuring vessel has a length of less than or equal to 100 mm, and wherein the optical article has a length corresponding to that of the hollow tube.

11. The method according to claim 1, wherein an internal surface of the hollow tube comprises elements in relief, and wherein the optical article is in contact with the internal surface of the hollow tube only at the elements in relief.

* * * * *